United States Patent [19]

Davidson et al.

[11] Patent Number: 5,185,161

[45] Date of Patent: * Feb. 9, 1993

[54] DISINFECTION METHOD AND COMPOSITION THEREFOR

[75] Inventors: Eugene A. Davidson, Hummlestown, Pa.; Robert D. Kross, Bellemore, N.Y.

[73] Assignee: Alcide Corporation, Norwalk, Conn.

[*] Notice: The portion of the term of this patent subsequent to Jan. 22, 2008 has been disclaimed.

[21] Appl. No.: 618,729

[22] Filed: Nov. 27, 1990

Related U.S. Application Data

[63] Continuation of Ser. No. 420,651, Oct. 11, 1989, Pat. No. 4,986,990, which is a continuation of Ser. No. 850,009, Apr. 10, 1986, abandoned, which is a continuation-in-part of Ser. No. 790,436, Oct. 23, 1985, abandoned, which is a continuation of Ser. No. 591,787, Mar. 21, 1984, abandoned.

[51] Int. Cl.$^5$ .............................................. A61K 33/14
[52] U.S. Cl. .................................................... 424/665
[58] Field of Search ................................ 424/149, 665

[56] References Cited

U.S. PATENT DOCUMENTS

| | | |
|---|---|---|
| Re. 31,779 | 12/1984 | Alliger .................... 252/187.23 |
| 2,071,091 | 2/1937 | Taylor ........................ 424/149 |
| 2,095,092 | 10/1937 | Barton ........................ 424/328 |
| 2,253,368 | 8/1941 | Dubeau ....................... 424/149 |
| 2,255,694 | 9/1941 | Beale .......................... 424/328 |
| 2,332,180 | 10/1943 | Soule .......................... 424/149 |
| 2,484,637 | 10/1949 | Mattocks et al. ............ 167/63 |
| 2,550,622 | 4/1951 | Taub ........................... 167/63 |
| 2,701,782 | 2/1955 | Culter ......................... 167/56 |
| 2,726,982 | 12/1955 | Ochs et al. .................. 167/58 |
| 2,842,422 | 7/1958 | Mosse ........................... 8/108 |
| 3,065,040 | 11/1962 | Wailbel ......................... 23/85 |
| 3,186,869 | 6/1965 | Friedman ................. 117/138.8 |
| 3,271,242 | 9/1966 | McNicholas .................. 8/108 |
| 3,297,578 | 1/1967 | Crutchfield et al. ........ 252/99 |
| 3,386,915 | 6/1968 | Rutschi et al. ............. 424/149 |
| 3,518,343 | 6/1970 | Welsh et al. ................. 424/53 |
| 3,663,716 | 5/1972 | Stolar ......................... 424/243 |
| 3,754,079 | 8/1973 | Callerame ................... 423/479 |
| 3,843,548 | 10/1974 | James ...................... 25/187 H |
| 3,950,554 | 4/1976 | Prince ........................ 424/270 |
| 4,035,483 | 7/1977 | Bunyan ...................... 424/149 |
| 4,067,962 | 1/1978 | Juneja ......................... 424/52 |
| 4,086,333 | 4/1978 | Bredwell .................... 424/130 |
| 4,104,190 | 8/1978 | Hartshorn .................. 424/149 |
| 4,296,102 | 10/1981 | Laso ........................... 424/130 |
| 4,296,103 | 10/1981 | Laso ........................... 424/130 |
| 4,303,546 | 12/1981 | Waegerle ................... 252/180 |
| 4,317,814 | 3/1982 | Laso ........................... 424/130 |
| 4,330,531 | 5/1982 | Alliger ....................... 424/149 |
| 4,388,204 | 6/1983 | Dimond et al. .............. 252/98 |
| 4,410,442 | 10/1983 | Lucas et al. ................ 424/326 |
| 4,507,285 | 3/1985 | Kuhne ........................ 424/130 |
| 4,547,381 | 10/1985 | Mason et al. ................ 426/16 |
| 4,554,091 | 11/1985 | Jones et al. ................. 252/187 |
| 4,585,482 | 4/1986 | Tice et al. ................... 424/149 |
| 4,690,772 | 9/1987 | Tell et al. ................... 424/149 |
| 4,696,811 | 9/1987 | Tatcliff ...................... 424/149 |

FOREIGN PATENT DOCUMENTS

| | | |
|---|---|---|
| 959238 | 12/1974 | Canada . |
| 965699 | 4/1975 | Canada . |
| 2329753 | 12/1973 | Fed. Rep. of Germany . |
| 58-18617 | 7/1981 | Japan . |
| 58-18616 | 2/1983 | Japan . |
| 158180 | 6/1972 | New Zealand . |
| 496247 | 11/1938 | United Kingdom . |
| 880507 | 10/1961 | United Kingdom . |

OTHER PUBLICATIONS

Chemical Abstracts No. 80:74331g (1974).
Chemical Abstracts No. 68:45873g (1968).
Gordon et al., "The Chemistry of Chlorine Dioxide," *Prog. Inorg. Chem.* 15:201, 1972.
Abstract (21 P 192) (JP Patent Kokai No. 58-18617).

*Primary Examiner*—S. J. Friedman
*Attorney, Agent, or Firm*—Seed & Berry

[57] ABSTRACT

There is disclosed, in one aspect, chlorous acid generating compositions useful for disinfecting substrates. The compositions comprise aqueous solutions containing a suitable amount of a protic acid, such as citric or malic acid, and a suitable amount of a metal chlorite, such as sodium chlorite. The chlorite ion concentration which is in the form of chlorous acid in the composition is no more than about 15 percent by weight of the total amount of chlorite ion concentration. In a preferred embodiment, the composition also contains a vicinal dihydroxy or polyhydroxy compound. In another preferred embodiment, the composition contains at least a 10-fold molar excess of a water soluble chloride ion compared to the total concentration of chlorite ion. In another aspect, there is disclosed a process for disinfecting substrates. This process comprises applying the compositions described above to a substrate. In yet another aspect, there is disclosed a process for preparing the compositions described above. This process comprises contacting the protic acid with the metal chlorite to form the disinfecting composition.

32 Claims, No Drawings

DISINFECTION METHOD AND COMPOSITION THEREFOR

CROSS-REFERENCE TO RELATED APPLICATIONS

This application is a continuation of U.S. patent application Ser. No. 07/420,651, filed Oct. 11, 1989, now U.S. Pat. No. 4,986,990, which is a continuation of U.S. patent application Ser. No. 06/850,009, filed Apr. 10, 1986, now abandoned, which is a continuation-in-part of U.S. Ser. No. 06/790,436, filed Oct. 23, 1985, now abandoned which is an continuation of U.S. Ser. No. 06/591,787, filed Mar. 21, 1984, now abandoned.

BACKGROUND OF THE INVENTION

This invention relates generally to compositions for disinfecting substrates as well as to processes for preparing and using such compositions.

The term "disinfectant" is used in this specification to broadly include any substance or composition that disinfects, sanitizes, deodorizes, sterilizes, or kills germs.

The use of chlorine compounds in various types of disinfectant compositions is well known. Chlorine compounds suggested for use in this regard include, for example, sodium hypochlorite, used in World War I as a wound irrigant, and chlorinated phenols such as m-chlorophenol. These compounds have increased bactericidal activity and reduced toxicity, in some instances, when compared to non-chlorinated phenols. Thus, m-chlorophenol has a phenol coefficient of 5.8 (S. aureus) to 7.4 (B. typhosus). Other chlorine compounds having some form of disinfectant utility include, for example, chlorine gas itself, chlorine dioxide, chloramine T, calcium hypochlorite (a standard swimming pool disinfectant), chloropicrin (a larvicide), chloroform (a fumigant), chlordane (an insecticide), and chloromycetin (an antibiotic).

Chlorine dioxide in particular has been found to be an especially effective disinfectant. This compound is quite versatile and has long been used as a bleaching agent such as in the oxidizing of the natural colorant present in cotton, wood pulp and other cellulosic fibrous material. In such uses, chlorine dioxide, though performing an oxidizing function, is nevertheless non-injurious with respect to the fibrous material.

Additionally, chlorine dioxide has long been used in the treatment of water supplies and a precursor is currently available commercially in powder form for use in swimming pools and in liquid form for household and industrial cleaning and disinfecting. In general, chlorine dioxide is superior to gaseous chlorine in the removal of odors and tastes, and in destroying and removing algae or other organic material. Moreover, chlorine dioxide is considered at least as effective as, if not superior to, chlorine gas as a bactericide, virucide or sporicide. Chlorine dioxide is further advantageous in that its antiseptic properties are not as sensitive to pH as chlorine-i.e., chlorine dioxide retains its disinfectant capacity to a significantly greater extent and over a wider pH range than does gaseous chlorine.

Despite the manifold advantages associated with the use of chlorine dioxide for the aforedescribed and related purposes, certain difficulties are nevertheless encountered in practice. Thus, chlorine dioxide as a concentrated gas is explosive and poisonous and accordingly is usually not shipped in the gaseous state to the medium or small user. It has thus become common practice to employ a chlorine dioxide-liberating compound such as sodium chlorite powder which is much safer from the standpoints of storage, shipping and handling. Generation of the chlorine dioxide from sodium chlorite or other chlorine dioxide liberating compound is usually effected by addition of acid, bleach (hypochlorite), or chlorine to the chlorine dioxide liberating compound.

The acid generation of chlorine dioxide is generally effected with the use of a relatively inexpensive inorganic acid, e.g., hydrochloric acid, sulfuric acid and the like. Other acids such as phosphoric or acetic acid (vinegar) have also been used.

Canadian Patent 959,238 to Callerame discloses such a conventional method of producing chlorine dioxide by reacting an alkali metal or alkaline earth metal chlorite, such as sodium chlorite, with an acid. In general, any acid may be used including strong acids such as sulfuric acid and hydrochloric acid and relatively weak acids such as citric and tartaric. This conventional method of producing chlorine dioxide ($ClO_2$) uses relatively high concentrations of chlorite and acid. The composition formed by this method is advantageous only for the immediate disinfection of a substrate-i.e., it does not result in a stable chlorine dioxide generating solution but instead provides a rapid generation of chlorine dioxide.

Acid-induced generation of chlorine dioxide from sodium chlorite as heretofore recommended and practiced has proven ineffective in that chlorine dioxide is not generated over an extended period of time. On the contrary, these compositions result in a relatively short concentrated period of chlorine dioxide generation and, once this gas dissipates, the residual system is not useful for disinfection purposes. One approach to compensate for this deficiency, and retain significant residual chlorine dioxide in solution formore prolonged activity is to use a system having an increased concentration of sodium chlorite and acid. This approach, however, may lead to toxicity problems, particularly when the composition is used in an enclosed air space. In addition, such a system would be inefficient, since the amount of chlorine dioxide produced greatly exceeds the amount needed for disinfection.

Another problem stems from the fact that the composition obtained from the interaction of the relatively high concentrations of sodium chlorite and acid materials used in the past can be injurious to health. Significantly, the toxicity problem imposes severe limitations on the general utility of the disinfectant composition, particularly with respect to the treatment of human beings.

These prior methods result in the nearly complete and rapid conversion of the majority of the chlorite precursor to chlorine dioxide which is then used as a gas, or in solution.

The above-noted problems with using chlorine dioxide as a disinfectant were solved to some extent by the use of a composition comprising a water soluble chlorite, such as sodium chlorite, and lactic acid. As disclosed in U.S. Pat. No. 4,084,747 to Alliger, this particular composition possesses improved disinfectant properties, properties not attained by using the same composition but replacing the lactic acid with other acids such as phosphoric acid, acetic acid, sorbic acid, fumaric acid, sulfamic acid, succinic acid, boric acid, tannic acid, and citric acid. It would be preferable from the standpoint of economics and acid availability to be able to use acids other than lactic acid, still obtain disinfectant utility, and maintain control over the rate of formation of chlorous acid and thereby chlorine dioxide.

The search has continued for improved compositions for disinfecting various germ carrying substances and improved disinfectant methods. This invention was made as a result of that search.

OBJECTS AND SUMMARY OF THE INVENTION

Accordingly, it is a general object of the present invention to avoid or substantially alleviate the above-identified problems of the prior art.

A more specific object of the present invention is to provide improved sanitizing, disinfecting and sterilizing compositions.

A further object of the invention is to provide such disinfecting compositions having negligible toxicity under conditions normally prescribed for use and thus highly useful in the germicidal treatment of substrates such as food receptacles and utensils, medical hardware, human or animal skin, and the like.

A further object of the present invention is to provide a process for disinfecting various substrates.

An additional object of the present invention is to provide a process for disinfecting substrates using compositions having negligible toxicity and controlled stability over a relatively wide pH range.

Other objects and advantages of the present invention will become apparent from the following summary of the invention and description of the preferred embodiments.

In one aspect, the present invention provides a composition for disinfecting a substrate using a chlorous acid generating composition. This composition comprises an aqueous solution containing a suitable amount of a protic acid, and a suitable amount of a metal chlorite. The chlorite ion concentration in the form of chlorous acid is no more than about 15 percent by weight of the total amount of chlorite ion concentration. The composition contains substantially no lactic acid, preferably no lactic acid at all.

In a preferred embodiment of this aspect of the present invention, there is provided a composition for disinfecting a substrate with a composition comprising a chlorous acid generating compound with a sufficient amount of a suitable organic acid to lower the pH of the composition to less than about 7. The suitable organic acid has the formula:

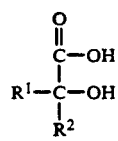

$R^1$ and $R^2$ may be the same or different and may be selected from the group consisting of hydrogen, methyl, —CH$_2$COOH, —CH$_2$OH, —CHOHCOOH, and —CH$_6$H$_5$. The pK of the organic acid is from about 2.8 to about 4.2. The composition contains substantially no lactic acid.

In a particularly preferred embodiment, the present invention provides a synergistic composition for disinfecting a substrate. This composition comprises
(a) a chlorine dioxide liberating compound:

(b) a sufficient amount of the suitable organic acid described above to lower the pH of the composition to less than about 7; and
(c) a vicinal dihydroxy or polyhydroxy compound.

In another aspect, the present invention provides processes for disinfecting a substrate using the compositions described above. These processes comprise applying the compositions described above to a substrate in order to disinfect the substrate.

In yet another aspect, the present invention provides a process for preparing these disinfecting compositions. This process comprises contacting the protic acid with the metal chlorite to form the disinfecting composition.

DETAILED DESCRIPTION OF THE PREFERRED EMBODIMENTS

As noted above, the present invention is directed to a chlorous acid generating composition for disinfecting a substrate. The composition comprises an aqueous solution containing a suitable amount of a protic acid, and a suitable amount of a metal chlorite such as sodium chlorite. The concentrations of chlorite and acid are relatively low and are such that the amount of the chlorite in the form of chlorous acid is no more than about 15 percent by weight of the total chlorite ion concentration in solution. Typically the amount of the chlorite in the form of chlorous acid is no more than about 10 percent by weight of the total chlorite ion concentration in solution.

The percent by weight of chlorite and chlorous acid may be calculated from the ionization constant of chlorous acid and the amount of hydrogen ion in solution produced by the partial ionization of the protic acid. Thus the hydrogen ion concentration, [H$^+$], in a solution of the protic acid, HA, of known molar concentration and whose ionization constant is K$_A$, may be calculated from the following relationship:

$$K_A = \frac{[H^+][A^-]}{[HA]}$$

This same relationship may be applied to calculate the relative chlorite and chlorous acid concentrations where the ionization constant for chlorous acid is $1.1 \times 10^{-2}$. That is:

$$1.1 \times 10^{-2} = \frac{[H^+][ClO_2^-]}{[HClO_2]}$$

where the hydrogen ion concentration, [H$^+$], is the quantity already determined by ionization of the known amount of the protic acid, HA. This calculation is well known to those skilled in this art.

The composition of this invention provides a metastable chlorous acid composition formed from relatively small amounts of chlorite and acid. This composition is capable of generating chlorine dioxide over a long period of time at continuing levels of effectiveness. As chlorine dioxide forms, more of the chlorite converts to chlorous acid by interacting with hydrogen ions further generated by ionization of the protic acid.

The compositions of this invention are therefore different from many prior art compositions which consist of relatively high concentrations of chlorite and acid. The prior art compositions result in the rapid conversion of chlorous acid to chlorine dioxide. The rate of chlorine dioxide formation depends on the sum of the square of chlorous acid concentration and the product of chlorous acid and chlorite concentrations according to the equation $$\frac{d[ClO_2^-]}{dt} = K_1[HClO_2]^2 + K_2[HClO_2][ClO_2^-]$$

See Gordon, "The Chemistry Of Chlorine Dioxide", 15 Prog. Inorg. Chem. 201 (1972).

Thus the rate at which chlorine dioxide forms depends exponentially on the amount of chlorite ion which is converted to chlorous acid and the amount of chlorite ion present.

In certain embodiments of the invention, the chlorous acid generating composition comprises an aqueous solution containing generally from about 0.01 to about 1, typically from about 0.02 to about 0.5, and preferably from about 0.03 to about 0.3 percent by weight of metal chlorite and a suitable amount of an organic acid having a pK of from about 2.8 to about 4.2. The pH of this composition is generally less than about 7, typically from about 2.2 to about 7.0.

In yet another embodiment of this invention, even lower concentrations of chlorite and acid may be used in the composition. These compositions comprise an aqueous solution containing generally up to about 0.3, and typically from about 0.0001 to about 0.03 percent by weight of metal chlorite, and a suitable amount of acid having a pK of from about 2.8 to about 4.2. The pH of the composition is generally less than about 7, typically from about 2.2 to about 7.0.

In certain embodiments of the invention, an acid is used of the formula

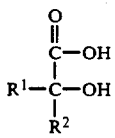

wherein $R^1$ and $R^2$ may be the same or different and may be selected from the group consisting of hydrogen, methyl, $-CH_2COOH$, $-CH_2OH$, $-CHOHCOOH$ and $-C_6H_5$.

Other embodiments of the invention may be formulated for a specific disinfecting procedure or as a result of a specific production method. These embodiments may contain an acid component, e.g. salicylic acid or carbonic acid, which is specifically suited for that procedure or production method.

Optionally the compositions of the invention may contain either a suitable amount of a compound containing vicinial hydroxy groups or an amount of a water soluble chloride in a significant molar excess to the chlorite, or both. These optional ingredients facilitate the formation of chlorine dioxide from chlorous acid and are thus useful in rapidly disinfecting compositions where an increased rate of chlorine dioxide formation is desired while maintaining a low concentration of chlorite and acid.

The metal chlorite useful in the present composition may more generally be described as a chlorine dioxide liberating compound. By "chlorine dioxide liberating compound" is meant any compound which, when appropriately treated, effects the production of chlorine dioxide as a result of a change in the valence state of the chlorine atom from +3 to +4. While any chlorine dioxide liberating compound may be used, water-soluble chlorites are preferred because they are readily available and inexpensive. Typical water-soluble chlorites include metal chlorites, such as alkali metal chlorites and alkaline earth metal chlorites. Sodium chlorite and potassium chlorite are preferred. Sodium chlorite is particularly preferred.

The disinfectant composition may be used in conjunction with an application medium. The application medium may be any compatible medium including a gel or a liquid such as water. An aqueous application medium is preferred. The application medium may contain other additives such as chelating agents (e.g., Na$_4$EDTA), surfactants (e.g., Pluronic F68 nonionic polyoxyalkylene or Nacconol alkylaryl sulfonate), or preservatives (e.g., sodium benzoate).

The amount of chlorine dioxide liberating compound that may be used in this composition may be generally from about 0.01% to about 1%, typically from about 0.02% to about 0.5%, and preferably from about 0.03% to about 0.3% by weight of the total composition (including the application medium).

At chlorite ion levels higher than about 0.5%, the concentration of chlorous acid formed upon admixture of a protic acid may be in excess of that required for the formation of a metastable chlorous acid solution. These higher concentrations of chlorous acid would cause the formation of chlorine dioxide, through the degradation of chlorous acid at too rapid a rate.

Any protic acid may be used in the present invention so long as the chlorite ion concentration limits described above are met. Suitable organic acids include citric, malic, tartaric, glycolic, mandelic or other structurally similar acids as described in Formula I hereinabove.

The pK of these organic acids may be generally from about 2.8 to about 4.2, and preferably from about 3.0 to about 4.0.

Salicylic acid and carbonic acid may also be used.

The amount of organic acid used in these compositions should be sufficient to lower the pH of the composition to less than about 7, typically from about 2 to about 5, and preferably from about 2.2 to about 2.7. Furthermore, this amount may be generally from about 0.01% to about 6%, typically from about 0.05% to about 3%, and preferably from about 0.1% to about 2% by weight of the total composition (including the application medium).

A suitable amount of a vicinal dihydroxy or polyhydroxy compound may also be added to the compositions of the present invention. The use of such compositions enables one to produce compositions according to the invention which are more rapidly effective in higher pH ranges. The use of these vicinal dihydroxy or polyhydroxy compounds also allows for the use of compositions according to the invention which contain a much lower acid concentration than that which is needed if the vicinal polyhydroxy compound comprising at least two vicinal hydroxy groups is absent.

Vicinal polyhydroxy compounds which contain at least two vicinal hydroxy groups are well known to those skilled in this art and include dextrose and other sugars, glycerin, sorbitol, inositols, and 1,2-propylene glycol. It is preferred that sugars with vicinal hydroxy groups in the cis configuration such as galactose, mannose, and ribose be used.

The use of such vicinal polyhydroxy compounds, particularly those with cis-vicinal hydroxy groups, in conjunction with the chlorine dioxide liberating compound and organic acid results in a synergistic composition. The vicinal dihydroxy or polyhydroxy compound catalyzes the formation of chlorine dioxide from chlorous acid. For example, the rate of formation of the active chlorine dioxide entity using a composition comprising sodium chlorite and mandelic acid is substantially enhanced by the addition of a relatively insubstantial amount of a vicinal polyhydroxy compound Thus, the use of as little as 0.1% ribose in the composition substantially enhances the rate of formation of the active entity vis-a-vis a composition containing only sodium chlorite and one of the organic acids discussed hereinabove.

Stated otherwise, a composition containing the vicinal polyhydroxy compound may be prepared having substantially the same initial germ-killing efficiency in a specified time period as a composition which does not contain the vicinal polyhydroxy compound even though the composition containing the polyhydroxy compound contains substantially much less organic acid and sodium chlorite. However, such activation of the system results in a more rapid depletion of the chlorite ion in the composition, so that the germ-killing activity at a later time period would be less.

The amount of vicinal polyhydroxy compound containing at least two vicinal hydroxy groups may vary widely, but in the present invention there is employed generally less than about 20%, typically from about 0.1% to about 10%, and preferably from about 0.2% to about 2% by weight of the total composition.

Alternatively, or in addition, the composition may contain a large excess of chloride ion in the form of an alkali or an alkaline earth metal salt. The excess may be from about a 10 to about a 100 fold excess by weight of chloride ion over total chlorite ion concentration. Large excesses of chloride ion in acid solutions (below a pH of about 7) cause the chlorite ion to decompose in an accelerated manner, via the formation of chlorous acid to form chlorine dioxide. In a preferred embodiment of the invention where rapid disinfection is required, the composition contains both a high excess of chloride ion and a sufficient amount of a vicinal polyhydroxy compound comprising at least two vicinal hydroxy groups.

The chlorine dioxide liberating compound is generally kept separate from the organic acid prior to use in order to avoid premature reaction of the ingredients.

The above-described compositions may be used to disinfect various substrates. The term "substrate" as used in the instant specification is intended to cover any type of surface or carrier which could provide a locus for the accumulation of germs (viruses, yeasts, bacteria, fungi, i.e., all types of microorganisms). Obvious examples include surgical and dental instruments, foods, food containers, human and animal skin, tissue, body fluids and mucous membranes, swimming pools, household sinks, garbage containers, bathroom appliances, etc.

Cleaning action may be enhanced by the addition of a wetting agent, the latter being compatible with and devoid of any tendency to react with chlorite, chlorous acid or chlorine dioxide. Particularly effective wetting agents for such use are anionic surfactants which are commercially available. The instant compositions in aerosol form may be effectively used to destroy airborne or atmospheric germs such as those carried within an enclosed air space.

When these compositions are used on human or animal skin, they may also be typically applied in conjunction with a gel application medium because of the ability of the gel to adhere to the skin. Any gelling agent or thickener which is non-toxic and non-reactive with the chlorine dioxide-liberating compound and organic acid may be used. Cellulose gels, particularly methyl and hydroxyethyl cellulose gels, polyvinylsulfonic acid, polyamide and silica-based gels, are preferred. Preservatives may also be used when the gel form is employed. For example, sodium benzoate may be used as a preservative in the organic acid gel.

The amount of thickener which may be used in the gel varies depending upon the intended application, the particular acid, the chlorine dioxide liberating compound, and the other additives employed. However, the amount may be generally from about 1 to about 30, typically from about 4 to about 20, and preferably from about 4 to about 6, percent by weight of the total composition. The amount of preservative in the total composition may be generally from about 0.01 to about 0.05, typically from about 0.01 to about 0.04, and preferably from about 0.02 to about 0.03, percent by weight of the total composition.

When the chlorine-dioxide liberating compound and organic acid are present in separate gels, the amounts of each present in the respective gels are adjusted so that when the gels are mixed the specified percentages will be present in the resulting composition. For example, when the gels are designed to be mixed in equal parts, which is preferred, the amount of chlorine dioxide liberating compound present in the first gel may be generally from about 0.02% to about 2%, typically from about 0.05% to about 1%, and preferably from about 0.1% to about 0.6% by weight of the first gel. The amount of organic acid present in the second gel may be from about 0.1% to about 12%, typically from about 0.5% to about 10%, and preferably from about 1% to about 6% by weight of the second gel.

Additionally, when the chlorine dioxide liberating compound and organic acid are present in separate gels, the preservative is present in only that gel which contains the organic acid and the thickener is present in both gels. The gel which contains the chlorine dioxide liberating compound is preserved by suitable alkaline pH adjustments.

Therefore, when the gels are designed to be mixed in equal parts, the amount of preservative present in the second gel, the organic acid gel, is generally from about 0.02% to about 0.1%, typically from about 0.02% to about 0.08%, and preferably from about 0.04% to about 0.06% by weight of the second gel. The amount of thickener present in both the first and second gels depends on the gelling agent and is generally from about 0.5 to about 15, and typically from about 2 to about 10, and preferably from about 2 to about 3, percent by weight of the individual gels.

These gels may be mixed just prior to application or may be simultaneously mixed and applied in situ.

The compositions of this invention may be applied to various substrates in a manner known to those skilled in this art. The compositions may be sprayed, coated or applied in any other manner depending upon the substrate being treated.

The compositions of this invention may be used for skin applications, for example, by applying a small but effective amount of the composition to the affected area of the skin using any means known to those skilled in this art including, for example, an applicator such as a cotton swab. The composition is allowed to remain on the affected area for a sufficient period of treatment. The composition may be reapplied to maintain an effective level of the composition throughout the period of treatment.

For most skin applications, a frequency of one or two applications provides relief. In most cases, the composition may be applied liberally to the site, preferably as soon as possible after the infection, disease, inflammation etc. appears. If liquid is applied, a suitable applicator is a cotton gauze soaked with a liquid formulation The lesion or affected area should be kept in contact with the wet gauze for a few minutes.

When gel is used, it should be liberally applied. If the gel is absorbed or accidentally removed, it may be reapplied as necessary.

These compositions may also be used in soap products, toothpastes, mouthwashes, and the like.

In addition to the gel and solution form, the chlorine dioxide liberating compound and the organic acid may also be provided in powder form in two packets or in a two compartment single package wherein the compartments are separated by a suitable seal. One embodiment of such a package uses a water soluble, heat sealable, polyvinyl-alcohol-cellulosic as the package material. Other suitable packaging materials compatible with the composition ingredients are well known to those skilled in this art.

The present invention is illustrated by the following Examples. All parts and percentages in the Examples as well as the specification and claims are by weight unless specified otherwise.

EXAMPLE I

This example illustrates the use of the present composition as a mouthwash.

A first solution is prepared by dissolving 0.4 grams of technical grade sodium chlorite, 0.17 grams of powdered $Na_4EDTA \cdot 4H_2O$, 0.5 grams of l-carvone (mint flavor) and the appropriate amount of a compatible food grade yellow dye in 500 milliliters of aqueous solution. A second solution is prepared by dissolving 1.375 grams of anhydrous citric acid and the appropriate amount of FD&C Blue #1 in a batch of 500 milliliters of a 10 percent by weight aqueous solution of glycerin.

The two solutions are mixed, preferably just prior to use, in substantially equal amounts and the mixture is used in the normal manner as a mouthwash. This results in improved bacterial, fungicidal, and taste properties over presently available commercial antiseptic mouthwashes and may aid in plaque reduction.

EXAMPLE II

This example illustrates the preparation of compositions capable of very rapid disinfection of contact lenses The lens may be immersed in the solutions of these compositions for several minutes, and upon removal can be immediately and safely placed on the eye.

The contact lens disinfectant solutions comprise sodium chlorite powder; citric (or equivalent) acid powder to convert sodium chlorite to chlorous acid; sodium chloride in sufficient quantity to render the final solution isotonic with tears and hasten the degradation of chlorous acid to chlorine dioxide; and optionally a sugar such as ribose which catalyzes the conversion of chlorous acid to chlorine dioxide. Other optional ingredients, such as polyvinyl alcohol or hydroxyethylcellulose, to modify the viscosity of the final solution, may also be used.

With such a combination, the initial solution formed by dissolving the materials in water will have a pH of less than about 4, but will rise to a pH of over about 5 within ten minutes, and to a pH of over about 6 within about one hour. This occurs because the citric acid transfers ionizable hydrogen atoms to sodium chlorite thereby forming chlorous acid and sodium dihydrogen citrate. Large excesses of chloride ion with respect to chlorite ion in acid solutions (below about pH 7) cause the chlorite ion to decompose, via the formation of chlorous acid, to form chlorine dioxide. In the process the acidity of the solution decreases, and the pH rises. Sugars such as ribose also catalyze the formation of chlorine dioxide from chlorous acid, and also diminish the acidity of the aqueous system. One of the end products of the formation of chlorine dioxide from chlorous acid is chloride ion. The chloride ion so formed increases the chloride ion pool already present and further causes the chlorite ion to decompose.

The chlorine dioxide thus rapidly generated from this mixture in combination with the remaining chlorite ion in this system provides highly effective microbiocidal activity, and kills microorganisms commonly found as contact lens contaminants.

The following two-part system, when combined in 50 ml of water, killed over $10^7$ cfu/ml of *Serratia marcescens*, and over $10^4$ cfu/ml of *Aspergillus fumigatus* within 30 seconds.

| Part A: | 5.0 mg Sodium chlorite |
| | 200.0 mg Sodium chloride |
| Part B: | 0.627 mg Citric acid, anhydrous |
| | 200.0 mg Sodium chloride |
| | 250.0 mg Ribose |

A contact lens placed in this prepared solution for only a few minutes would be disinfected and could be, placed back in the eye, with no further saline rinse, and with full comfort and safety.

The above solution could also be prepared by combining the ingredients, without sodium chloride, in a pre-existing saline solution, and the results would be substantially the same.

If a sugar such as ribose were not used, a slightly higher level of citric acid (or equivalent) could be used. The same type of pH rise would occur, although more slowly, and the final pH would not be as high (between about pH 4.5 and 5.5). In this embodiment, it may be necessary to employ a subsequent sterile saline wash if it is desired to reinsert the lens within a few minutes of disinfection.

EXAMPLE III

This Example illustrates the use of the compositions of the present invention as a unique therapeutic agent for the treatment of acne.

Salicylic acid is currently used in topical acne agents as a comedolytic agent. As a comedolytic, salicylic acid loosens and strips away tissue from comedones, the plugged sebaceous gland involved in the pathogenesis of acne.

The present invention uses salicylic acid, which has a pK of 2.97, as a hydrogen ion source to convert some of the chlorite ion to chlorous acid and then to the freeradical ClO₂. The system therefore provides in addition to the comedolytic activity of the salicylic acid the bactericidal activity of the chlorine dioxide/chlorous acid system.

In a preferred embodiment of the invention, the following two part formulation is a composition useful for topically treating acne:

| Acne Gel | |
|---|---|
| | Per Cent by Weight |
| Part I | |
| Salicylic Acid | 2.0% |
| Isopropyl Alcohol | 30.0% |
| Sodium Benzoate | 0.04% |
| Natrosol 250 MR | 2.1% |
| Pluronic F 68 | 0.4% |
| Deionized Water | q.s. |
| Part II | |
| Rheothik 80-11 | 45.0% |
| Sodium hydroxide, 1N | 38.0% |
| Nacconol 90-F | 1.8% |
| Na₄ EDTA (38%) | 0.5% |
| Sodium Chlorite (79%) | 0.4% |
| Deionized Water | q.s. |

Natrosol 250 MR is a variety of hydroxyethyl cellulose. Pluronic F68 is a non-ionic surface active agent. Rheothik 80-11 is a polyvinylsulfonic acid gelling agent and Nacconol 90-F is an anionic surface active agent. Other varieties of these optional ingredients having the equivalent or similar properties may be substituted in the above formulation and used in accordance with the invention.

EXAMPLE IV

This example illustrates the preparation of carbonic acid compositions.

Carbon Dioxide gas, when dissolved in water, forms carbonic acid, i.e.

$$CO_2 + H_2O \rightleftharpoons H_2CO_3$$

Carbonic Acid is capable of dissociating in water to provide hydrogen ion and bicarbonate ion, i.e.

$$H_2CO_3 \rightleftharpoons H^+ + HCO_3^- \quad pK = 6.37$$

If a sodium chlorite solution is placed in a sealed vessel into which a gas can be introduced under pressure, e.g. a sealed soda dispenser, and then a CO₂ cartridge is expelled into the solution, the above two reactions will ensue, and some liberated hydrogen ion will react with the chlorite ion to form chlorous acid, i.e., $$H^+ + ClO_2^- \rightleftharpoons HClO_2$$

The chlorous acid, in the acid environment, will slowly disproportionate to form the disinfecting material, chlorine dioxide, by one of several reactions, e.g., $$5\ HClO_2 \rightarrow 4ClO_2 + HCl + 2H_2O$$

$$4\ HClO_2 \rightarrow 2ClO_2 + HCl + HClO_3 + H_2O$$

Accordingly, by releasing this pressurized solution into the environment, there is provided a disinfecting solution containing chlorine dioxide. The pressurized solution is stable for at least several weeks.

Not only can the solution be used to disinfect substrates, but the solution itself is also disinfected. To illustrate, a CO₂ cartridge, containing 5.36 grams of the compressed CO₂ gas, is discharged under its own pressure into one liter of solution containing 0.0103 percent sodium chlorite. The pH of the solution, prior to CO₂ charging, is 6.45. At various times thereafter, the level of ClO₂ is measured spectrophotometrically. The pH of the solution is also measured and these measurements are shown in the Table below.

| Time (hours) | pH | ClO₂ (ppm) |
|---|---|---|
| 0 | 6.45 | — |
| 4 | 4.85 | 1.1 |
| 24 (1 day) | 4.2 | 1.7 |
| 96 (4 days) | 4.0 | 2.7 |
| 240 (12 days) | 4.0 | 5.0 |
| 336 (16 days) | 4.0 | 8.8 |

These concentrations of chlorine dioxide are highly effective for destroying a wide range of bacteria, yeasts, fungi and viruses.

One specialized application of this system is in the disinfection of contact lenses. Immersion of a contaminated lens, particularly a hydrophilic lens, into such a solution for a few minutes may destroy the contaminating organisms. If the chlorite solution contained the appropriate amount of sodium chloride as well (i.e. physiological saline), the disinfected lens could be placed in the eye without a subsequent saline rinse. The chloride ion would also hasten the conversion of the chlorite to chlorine dioxide. The further addition to this mixture of a small quantity, e.g. 0.01-0.1%, of a vicinal cis-hydroxy sugar (e.g. ribose, galactose) would additionally hasten the conversion of chlorite to ClO₂.

Another particular application of this embodiment is in the preparation of potable water. By discharging a CO₂ cartridge into a pressure bottle containing water of suspect quality (e.g. the water one might find during a camping trip), to which a small amount of chlorite powder is added, a supply of potable water is obtained. The quantity of chlorite powder is selected in order to provide adequate disinfection without leaving levels of chlorite which might be considered harmful, or providing levels of ClO₂ of a similar nature. The addition of a small quantity of cis-hydroxy sugar to provide more rapid and more complete conversion of chlorite to ClO₂ facilitates the use of lower initial chlorite levels.

The principles, preferred embodiments and modes of operation of the invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

We claim:

1. A process for disinfecting a substrate comprising contacting said substrate with an aqueous solution consisting essentially of from about 0.01% to about 6% by weight of an organic acid, wherein the pK of the organic acid is from about 2.8 to about 4.2, and wherein the organic acid is not lactic acid, and from about 0.0001% to about 0.45% by weight based upon the total weight of said composition of a metal chlorite, such that the chlorite ion concentration in the form of chlorous acid is not more than about 15% by weight of the total amount of chlorite ion concentration.

2. The process of claim 1 wherein the metal chlorite is sodium chlorite.

3. The process of claim 1 wherein the organic acid is selected from the group consisting of citric acid, malic acid, tartaric acid, glycolic acid, mandelic acid, salicylic acid, carbonic acid, and combinations thereof.

4. The process of claim 1 wherein the organic acid is citric acid.

5. A process for disinfecting a substrate comprising contacting said substrate with an aqueous solution consisting essentially of from about 0.01% to about 6% by weight glycolic acid, and from about 0.01% to about 0.45% by weight based upon the total weight of said composition of a metal chlorite, such that the chlorite ion concentration in the form of chlorous acid is not more than about 15% by weight of the total amount of chlorite ion concentration.

6. The process of claim 5 wherein glycolic acid ranges from about 0.05% to about 3% by weight of the total composition.

7. The process of claim 5 wherein glycolic acid ranges from about 0.1% to about 2% by weight of the total composition.

8. The process of claim 5 wherein the metal chlorite ranges from about 0.03% to about 0.3% by weight of the total composition.

9. The process of any one of claims 5-8 wherein the metal chlorite is sodium chlorite.

10. The process of claim 1 wherein the substrate is selected from skin, tissue, body fluids and mucous membranes.

11. A process for disinfecting a substrate comprising contacting said substrate with an aqueous solution consisting essentially of from about 0.01% to about 6% by weight of an organic acid, wherein the pK of the organic acid is from about 2.8 to about 4.2, and wherein the organic acid is not lactic acid, and from about 0.01% to about 0.45% by weight based upon the total weight of said composition of a metal chlorite, such that the chlorite ion concentration in the form of chlorous acid is not more than about 15% by weight of the total amount of chlorite ion concentration.

12. The process of claim 11 wherein the organic acid ranges from about 0.05% to about 3% by weight of the total composition.

13. The process of claim 11 wherein the organic acid ranges from about 0.1% to about 2% by weight of the total composition.

14. The process of claim 11 wherein the metal chlorite ranges from about 0.03% to about 0.3% by weight of the total composition.

15. The process of any one of claims 11-14 wherein the metal chlorite is sodium chlorite.

16. The process of any one of claims 11-14 wherein the organic acid is selected from the group consisting of citric acid, malic acid, tartaric acid, glycolic acid, mandelic acid, salicylic acid, carbonic acid, and combinations thereof.

17. The process of claim 11 wherein the substrate is selected from skin, tissue, body fluids and mucous membranes.

18. A chlorous acid generating composition comprising an aqueous solution consisting essentially of from about 0.01% to about 6% by weight of an organic acid, wherein the pK of the organic acid is from about 2.8 to about 4.2, and wherein the organic acid is not lactic acid, and from about 0.0001% to about 0.45% by weight based upon the total weight of said composition of a metal chlorite, such that the chlorite ion concentration in the form of chlorous acid is not more than about 15% of weight of the total amount of chlorite ion concentration.

19. The composition of claim 18 wherein the metal chlorite is sodium chlorite.

20. The composition of claim 18 wherein the organic acid is selected from the group consisting of citric acid, malic acid, tartaric acid, glycolic acid, mandelic acid, salicylic acid, carbonic acid, and combinations thereof.

21. The composition of claim 18 wherein the organic acid is citric acid.

22. A chlorous acid generating composition comprising an aqueous solution consisting essentially of from about 0.01% to about 6% by weight of an organic acid, wherein the pK of the organic acid is from about 2.8 to about 4.2, and wherein the organic acid is not lactic acid, and from about 0.01% to about 0.45% by weight based upon the total weight of said composition of a metal chlorite, such that the chlorite ion concentration in the form of chlorous acid is not more than about 15% by weight of the total amount of chloride ion concentration.

23. The composition of claim 22 wherein the organic acid ranges from about 0.05% to about 3% by weight of the total composition.

24. The composition of claim 22 wherein the organic acid ranges from about 0.1% to about 2% by weight of the total composition.

25. The composition of claim 22 wherein the metal chlorite ranges from about 0.03% to about 0.3% by weight of the total composition.

26. The composition of any one of claim 22-25 wherein the metal chlorite is sodium chlorite.

27. The composition of any one of claim 22-25 wherein the organic acid is selected from the group consisting of citric acid, malic acid, tartaric acid, glycolic acid, mandelic acid, salicyclic acid, carbonic acid, and combinations thereof.

28. A chlorous acid generating composition comprising an aqueous solution consisting essentially of from about 0.01% to about 6% by weight glycolic acid, and from about 0.01% to about 0.45% by weight based upon the total weight of said composition of a metal chlorite, such that the chlorite ion concentration in the form of chlorous acid is not more than about 15% by weight of the total amount of chlorite ion concentration.

29. The composition of claim 28 wherein glycolic acid ranges from about 0.05% to about 3% by weight of the total composition.

30. The composition of claim 28 wherein glycolic acid ranges from about 0.1% to about 2% by weight of the total composition.

31. The composition of claim 28 wherein the metal chlorite ranges from about 0.03% to about 0.3% by weight of the total composition.

32. The composition of any one of claims 28-31 wherein the metal chloride is sodium chlorite.

* * * * *